United States Patent [19]

Oji et al.

[11] Patent Number: 5,116,621
[45] Date of Patent: May 26, 1992

[54] ANTI-INFLAMMATORY ANALGESIC PATCH

[75] Inventors: Akihito Oji, Ohkawa; Yukihiro Tada, Takamatsu; Noriyuki Sasaki, Shiki; Mitsuo Mizumura, Kawagoe, all of Japan

[73] Assignees: Lederle (Japan), Ltd., Tokyo; Teikoku Seiyaku Co., Ltd., Kagawa, both of Japan

[21] Appl. No.: 633,146

[22] Filed: Dec. 24, 1990

[30] Foreign Application Priority Data

Dec. 25, 1989 [JP] Japan .................... 1-332599

[51] Int. Cl.$^5$ ............................ A61F 13/00
[52] U.S. Cl. ...................... 424/445; 424/449; 424/448; 424/447
[58] Field of Search .......... 424/445, 448, 449

[56]  References Cited

U.S. PATENT DOCUMENTS

| 4,008,321 | 2/1977 | Kamishita et al. | 424/445 |
| 4,534,980 | 8/1985 | Itoh et al. | 424/445 |
| 4,911,916 | 3/1990 | Cleary | 424/448 |
| 4,954,343 | 9/1990 | Hosaka et al. | 424/449 |
| 4,971,799 | 11/1990 | Nakagawa et al. | 424/448 |
| 4,978,531 | 12/1990 | Yamazaki et al. | 424/449 |

FOREIGN PATENT DOCUMENTS 0127840 12/1984 European Pat. Off. .
0156565 10/1985 European Pat. Off. .
0338291 10/1989 European Pat. Off. .

*Primary Examiner*—Thurman K. Page
*Assistant Examiner*—Leon R. Horne
*Attorney, Agent, or Firm*—Wegner, Cantor, Mueller & Player

[57] ABSTRACT

An anti-inflammatory analgesic patch having a drug reservoir layer comprising 4-biphenylylacetic acid as the effective ingredient, a homo- and/or co-polymer of acrylic acid and ordinary adjuvants such as a shape-retaining agent, humectant, thickener, etc., which is characterized in that said drug reservoir further contains crotamiton and pH of the drug reservoir is adjusted within a range of 6 to 8 with a water-soluble organic amine and an organic acid.

9 Claims, 3 Drawing Sheets

ANTI-INFLAMMATORY ANALGESIC PATCH

DETAILED EXPLANATION OF THE INVENTION

This invention relates to an anti-inflammatory analgesic patch. More specifically the invention relates to an anti-inflammatory analgesic patch containing 4-biphenylylacetic acid as the effective ingredient and crotamiton as an absorption assistant.

4-Biphenylylacetic acid is an active metabolite of fenbufen which is an oral non-steroidal anti-inflammatory, analgesic drug, and is itself known to exhibit strong anti-inflammatory and analgesic actions. It is also known, however, that oral administration of 4-biphenylylacetic acid may sometimes be accompanied by ulceration or bleeding of digestive organs. Hence, in spite of its excellent anti-inflammatory and analgesic activities, it has not yet been used in clinical therapy as an oral administration drug.

Studies had been therefore made for medical formulation of 4-biphenylylacetic acid which will allow effective utilization of its strong acitivities, and consequently it was proposed to transdermally administer it as a gel-type ointment (cf. EP-A-127840, U.S. Pat. No. 4533546), allowing its introduction as a therapeutically practical formulation.

On the other hand, research has been widely made heretofore for formulations for transdermal administration of oral non-steroidal anti-inflammatory and analgesic drugs, and patches were proposed as a suitable form. Thus as for 4-biphenylylacetic acid also a patch formulation was proposed (cf. Japanese Official KOKAI Gazette, Laid-open No. 85913/89), in which an alkali and a water-soluble organic amine are contained with the view to secure solubility of 4-biphenlylacetic acid as the active ingredient. However, the patches actually obtained are sticky and frequently cause oozing. Furthermore the 4-biphenylylacetic acid therein tends to be crystallized and precipitated in the drug reservoir. Thus the product is not necessarily regarded effective for the activity retention of 4-biphenylylacetic acid.

The present inventors therefore conducted an extensive study for formulating a practical patch which will allow full exhibition of the strong anti-inflammatory and analgesic effects of 4-biphenylylacetic acid.

Those patches which are normally referred to as cataplasms conventionally contain as the chief component an inorganic matter like kaolin which contain such ingredients of the base as shape-retaining agents like purified gelatin; humectants like glycerin and propylene glycol; thickeners like carboxymethylcellulose sodium (CMC-Na) and sodium polyacrylate, etc. The base is then blended with an active component as the chief drug and the blend is spread on knitted or non-woven fabric. In the occasion of preparing a transdermal patch containing 4-biphenylylacetic acid, if the active component is simply blended with such conventional patch base, it is adsorbed by the inorganic matter like kaolin and cannot be released, which markedly reduces the transdermal absorption of the component. Furthermore, the CMC-Na or sodium polyacrylate blended as a thickener reacts with the 4-biphenylylacetic acid to harden the drug reserver. Consequently tackiness of the drug reservoir layer is impaired to lose its function as a transdermal patch. Thus it was discovered that the practice only provided an unsatisfactory transdermal patch containing 4-biphenylylacetic acid.

In accordance with the invention, it has been found that if no inorganic matter like kaolin is used as an ingredient of the base and a homo- and/or co-polymer of acrylic acid is used as the thickener, such base is blended with 4-bi-phenylylacetic acid and crotamiton and furthermore if pH of the drug reservoir is adjusted to a range of 6 to 8 with a water-soluble organic amine and an organic acid, said homo- and/or co-polymer exhibit stable gel property to provide an anti-inflammatory analgesic patch excelling in durability of medical efficacy of 4-biphenylyl-acetic acid and allowing quantitative administeration. Furthermore the patch itself exhibits stable tackiness and causes little skin-irritation.

Accordingly, therefore, the present invention provides an anti-inflammatory analgesic patch containing 4-biphenylylacetic acid having an excellent anti-inflammatory and analgesic activities as the effective medical component.

More specifically, the present invention provides an anti-inflammatory analgesic patch having a drug reservoir layer composed of 4-biphenylylacetic acid as the effective ingredient, homo- and/or co-polymer of acrylic acid as a thickener and other ordinary adjuvants like shape-retaining agent, humectant, etc., said patch being characterized in that the drug reservoir layer further contains crotamiton and pH of the drug reservoir layer is adjusted within a range from 6 to 8 with a water-soluble organic amine and organic acid.

The anti-inflammatory analgesic patch of the present invention exhibits stable and good gel property because the polyacrylic acid and/or polyacrylate copolymer contained as a base ingredient is neutralized with a water-soluble organic amine. The neutralization furthermore imparts excellent tackiness to the drug reservoir itself. At the same time, the crotamiton contained as an absorption assistant promotes release of 4-biphenylyl-acetic acid which is the active component, and consequently allows the patch to exhibit superior anti-in-flammatory and analgesic effect over many hours.

Polyacrylic acid and/or polyacrylate copolymer blended as a base ingredient of the patch of the present invention serve as a thickener for imparting tackiness to the drug reservoir itself.

Examples of polyacrylic acids include water-soluble acrylic acid homopolymers having a number average molecular weight of about 30,000 to about 500,000. Polyacrylate copolymers useful for the present invention include water-soluble carbonyl-containing copolymers of acrylic acid with other vinyl monomers copolymerizable therewith, such as the alkenylethers obtained by allylating polyhydroxy alcohols like sucrose, oligose, aldohexose, ketohexose, butane-triol, etc. Such copolymers can have a number average molecular weight of about 1,000,000 to about 3,000,000, specific examples including KIVISWAKO ®-103, 104 or 105 (products of WAKO JUNYAKU KOGYO Co. Ltd.), CARBOPOL ®-934, 940 or 941 (products of GOODRICH Co. Ltd.).

These polyacrylic acids and polyacrylate co-polymers can be each singly blended to impart tackiness to the drug reservoir, while it is likewise possible to use them concurrently to secure the intended tackiness. It was found that the single use of polyacrylic acid or concurrent use of a large amount of polyacrylic acid increases the tackiness of the drug reservoir, while single use or concurrent use of a large amount of poly-acrylate copolymer increases shape-retaining property of the drug reservoir per se.

Therefore the tackiness and shape retaining property of the drug reservoir can vary depending on the amount of polyacrylic acid and/or polyacrylate copolymer. The amount of polyacrylic acid, when used alone, is 0.2 to 10%, preferably 0.5 to 6%, more preferably 1 to 4%, based on the weight of the drug reservoir, while that of polyacrylate copolymer, when used alone, can range from 0.5 to 10%, preferably 1.5 to 8%, more preferably 2 to 5%, based on the weight of the drug reservoir, the percentages being by weight.

When both polyacrylic acid and polyacrylate copolymer are used, their respective amount may be within the above-specified range, to make the total 1 to 10%, preferably 1.5 to 8%, more preferably 2 to 5%, the percentages being by weight, based on the weight of the drug reservoir.

When polyacrylic acid and polyacrylate copolymer are used concurrently, their blend ratio is not critical, but generally polyacrylic acid/polyacrylate copolymer, by weight ratio, can range conveniently from 5/1 to 1/5, preferably from 3/1 to ⅓.

The stable gel properties desirable for drug reservoir of the patch of the present invention can be still improved by neutralizing the polyacrylic acid and/or polyacrylate copolymer blended as one of the base ingredients with water-soluble organic amines.

Illustrative of the water-soluble organic amines used in the patch of the invention are mono(lower alkanol)amines such as monomethanolamine, monoethanolamine, monopropanolamine and monoisopropanolamine; di-(lower alkanol)amines such as dimethanolamine, diethanolamine, dipropanolamine, diisopropanolamine, dibutanolamine, diisobutanolamine and di-sec-butanolamine; tri-(lower alkanol)amines such as trimethanolamine, tri-ethanolamine, tripropanolamine, triisopropanolamine, tributanolamine, triisobutanolamine and tri-sec-butanolamine; mono(lower alkyl)amines such as methylamine, ethylamine, propylamine and isopropylamine; di(lower alkyl)amines such as dimethylamine, diethylamine, dipropylamine diisopropylamine; and tri(lower alkyl)amines such trimethylamine, triethylamine, tripropylamine and triisopropylamine. Of these, the mono-, di- and tri-(lower alkanol) amines are preferred, and diisopropanolamine, triethanolamine and diethanolamine are especially preferred. These amines may be used singly or in combination.

The water-soluble organic amine is used in an amount larger than that required to neutralize the polyacrylic acid and/or polyacrylate copolymer in the drug reservoir, which amount can conveniently range from 0.5 to 15%, preferably from 0.5 to 10%, more preferably from 1 to 7%, the percentages being by weight, based on the weight of the drug reservoir, although it may vary depending on the kind of specific amine or amines used, the amount of 4-biphenylylacetic acid and the amount of the polyacrylic acid and/or polyacrylate copolymer. The pH of the drug reservoir layer of the patch of the invention is adjusted to a range 6-8, preferably 6.3-7.5, more preferably 6.5-7.3, by concurrent use of an organic acid or acids with the water-soluble organic amine or amines. This adjustment is essential for reducing skin irritation when the patch is stuck on skin, improving stability of the formulation and maintaining tackiness of the drug reservoir layer.

Examples of useful organic acids include malic acid, oleic acid, tartaric acid, lactic acid, gluconic acid and citric acid. The amount of these organic acids is not critical, but for adjusting the pH of the drug reservoir to afore-specified range, it may normally be from 0.1 to 5%, preferably from 0.1 to 3%, more preferably from 0.2 to 1%, the percentages being by weight, based on the weight of the drug reservoir.

The amount of 4-biphenylylacetic acid, the effective ingredient of the anti-inflammatory analgesic patch of the present invention, to be blended is not subject to any general limitation, it being sufficient that the amount be enough for the patch to exhibit the intended anti-inflammatory and analgesic effect. Normally, however, it is suitably from 0.1 to 5%, preferably from 0.3 to 3%, more preferably from 0.4 to 2%, the percentages being by weight, based on the total weight of the drug reservoir.

One of the unique features of the patch of the invention resides in that crotamiton is blended in the drug reservoir with a view to promoting the transdermal absorption of particularly 4-biphenylylacetic acid as the active component. While crotamiton has been conventionally used as a dissolution promotor, it has been found to act as a transdermal absorption assistant for 4-biphenyl-ylacetic acid in the patch of the present invention (cf. Comparative test given later).

The amount of crotamition as an absorption assistant may conveniently be at least 0.05 parts, per 100 parts of 4-bi-phenylylacetic acid, the parts being by weight, although it may vary depending on the amount of 4-biphenylylacetic acid in the drug reservoir layer, representative examples have 20, 40 and 50 parts crotamitan per 100 parts of 4-biphenylacetic acid.

The anti-inflammatory analgesic patch of the invention can further contain other ordinary adjuvants such as shape-retaining agent, humectant, etc.

For example, the patch can optionally contain such humectants as glycerin, sorbitol, propylene glycol, polyethylene glycol, 1,3-butanediol, etc. in addition to the foregoing components. Such humectants can be used either singly or in combination, whereby to keep the patch in moist state and maintain favorable mobility of 4-biphenylylacetic acid in the drug reservoir layer and to increase duration of its absorption. Generally preferred amount of such humectant or humectants is from 10 to 60% by weight, more preferably from 20 to 50% by weight, based on the weight of the drug reservoir.

The patch of the invention can furthermore optionally contain a shape-retaining agent such as purified gelatin, carboxymethylcellulose sodium (CMC-Na), etc. The amount of such shape-retaining agent can generally range from 0.1 to 10% by weight, particularly from 0.5 to 5% by weight, based on the weight of the drug reservoir.

The transdermal patch of the invention may further contain other pharmaceutically acceptable thickeners such as carboxymethylcellulose sodium or sodium polyacrylate; or pharmaceutically acceptable preservatives such as esters of paraoxybenzoic acid or sorbic acids in appropriate combination.

The drug reservoir layer in the patch of the invention allows stable dissolution of the effective component, 4-biphenylylacetic acid, in the drug reservoir, preventing its precipitation thereinto as crystals. Consequently, the bioavailability of the effective component in the patch is extremely high.

According to the present invention, the drug reservoir containing 4-biphenylylacetic acid is spread on a surface of a sheet-formed backing like fabric, paper, etc. While the spreading method and thickness of the spread layer are subject to no critical limitation, it is preferred to make the drug reservoir in the patch relatively thick, e.g., at least 0.5 mm, because in such a case the drug reservoir layer itself exhibits an ODT (occlusion dressing technique) effect and improves the bioavailability of 4-biphenylylacetic acid.

The material to be used as the sheet-formed backing neither is critical, but any of those ordinarily used for transdermal patches can be used.

The transdermal patch containing 4-biphenylylacetic acid of the present invention improved the releasing ability and durability of 4-biphenylylacetic acid by blending as a base ingredient of the patch polyacrylic acid and/or polyacrylate copolymer which have been heretofore used for base component of gel ointment and known to have good releasing ability of medical ingredient, and by regulating the pH of the drug reservoir to 6-8, whereby improving the stability and adhesiveness of the patch.

Furthermore, according to the present invention crotamiton is blended to achieve the effect of promoting transdermal absorption of 4-biphenylylacetic acid. Thus the bioavailability of 4-biphenylylacetic acid is markedly improved compared to the case of simply blending it with conventional base ingredients of transdermal patch.

According to the patch of the invention, therefore, the dose of 4-biphenylylacetic acid to be administered can be determined easily and with certainty from the surface area of the patch, and by suitably cutting the patch to the size appropriate for individual patient's condition and applying it to the patient's skin, the active ingredient can be quantitatively administered. Again, because it can be administered by intimately adhering the patch to the affected part, the action of 4-biphenylylacetic acid can be maintained over a prolonged period.

Hereinafter the present invention will be more specifically explained referring to working examples and biological activity test of the formulations, it being understood that the scope of the invention is in no way restricted thereby.

EXAMPLE 1

Figure 1:
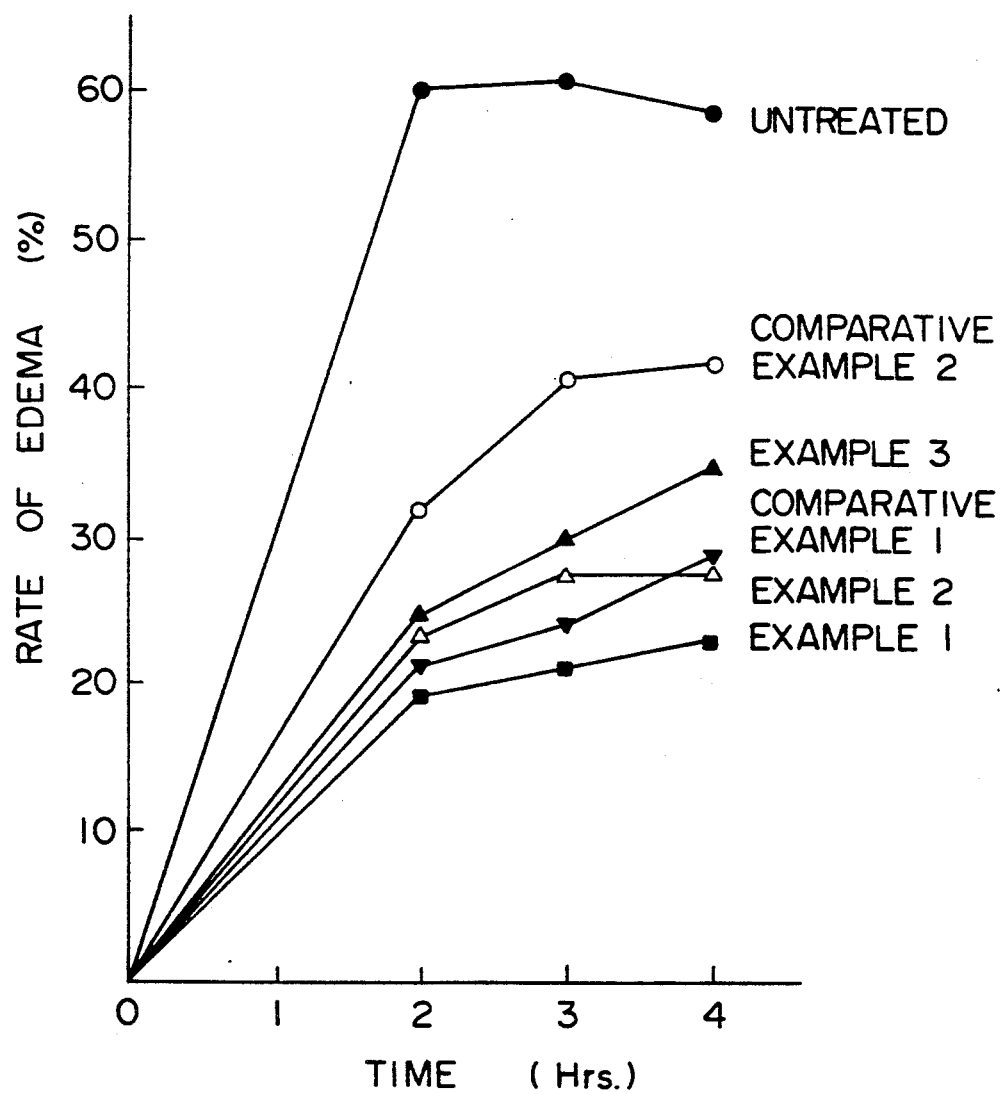
FIG. 1 shows the rate (%) of carrageenin-induced paw edema of rats measured in Test 1.

| 4-biphenylylacetic acid | 1 g |
|---|---|
| crotamiton | 0.5 g |
| diisopropanol amine | 3 g |
| sodium polyacrylate | 2 g |
| purified gelatin | 1 g |
| polyvinyl alcohol | 0.5 g |
| polyacrylate copolymer | 2.5 g |
| glycerin | 20 g |
| D-sorbitol solution | 20 g |
| aluminum hydroxide hydrate | 0.5 g |
| tartaric acid | 0.3 g |
| methylparaben | 0.1 g |
| propylparaben | 0.05 g |
| purified water | q.s. 100 g |

The polyacrylate copolymer was dissolved in 30 g of purified water. Separately, purified gelatin and polyvinyl alcohol were dissolved in the rest of purified water, and the solution was stirred at 60° C. The above two solutions were mixed. To the resultant solution, a mixture of crotamiton, diisopropanol amine and 4-biphenylylacetic acid was added. The mixture was kneaded sufficiently. To the mixture, D-sorbitol solution was added and then, glycerin in which aluminum hydroxide hydrate, sodium polyacrylate, tartaric acid, methylparaben and propylparaben were dispersed was added. The mixture was kneaded sufficiently until it became uniform to give a drug reservoir.

The drug reservoir was spread on a sheet of nonwoven fabric at 1,000 g/m$^2$, and was covered with a protective film. Then, it was cut into an appropriate size to make transdermal patches (pH 7.2).

| 4-biphenylylacetic acid | 1 g |
|---|---|
| crotamiton | 0.2 g |
| diisopropanol amine | 3 g |
| sodium polyacrylate | 1 g |
| polyacrylic acid | 1.5 g |
| polyacrylate copolymer | 1 g |
| glycerin | 20 g |
| propylene glycol | 5 g |
| aluminum acetate | 0.5 g |
| oleic acid | 0.5 g |
| methylparaben | 0.1 g |
| purified gelatin | 1 g |
| propylparaben | 0.05 g |
| purified water | q.s. 100 g |

The polyacrylate copolymer and polyacrylic acid were dissolved in 50 g of purified water. Separately, purified gelatin was dissolved in the rest of purified water, and the solution was stirred at 60° C. The above two solutions were mixed. To the resultant solution, a mixture of crotamiton, diethanolamine, 4-biphenylylacetic acid and oleic acid was added. The mixture was kneaded sufficiently. To the mixture, propylene glycol was added and then, glycerin in which sodium polyacrylate, aluminum acetate, methylparaben and propylparaben were dispersed was added. The mixture was kneaded sufficiently until it became uniform to give a drug reservoir.

The drug reservoir was spread on a sheet of nonwoven fabric at 1,000 g/m$^2$, and was covered with a protective film. Then, it was cut into an appropriate size to make transdermal patches (pH 7.0).

| 4-biphenylylacetic acid | 0.5 g |
|---|---|
| crotamiton | 0.2 g |
| triethanolamine | 3.5 g |
| sodium polyacrylate | 0.5 g |
| polyacrylic acid | 1 g |
| CMC-Na | 0.5 g |
| polyacrylate copolymer | 2 g |
| glycerin | 20 g |
| propylene glycol | 5 g |
| D-sorbitol solution | 15 g |
| aluminum chloride | 0.5 g |
| tartaric acid | 0.5 g |
| propylvinyl alcohol | 0.5 g |
| methylparaben | 0.1 g |
| propylparaben | 0.1 g |
| purified water | q.s. 100 g |

The polyacrylate copolymer and polyacrylic acid were dissolved in 40 g of purified water. Separately, polyvinyl alcohol was dissolved in the rest of purified water by heating. The above two solutions were mixed until it became uniform. To the resultant solution, a mixture of 4-biphenylylacetic acid, cortamiton, triethanolamine and propylene glycol was added. The mixture was kneaded sufficiently. To the mixture, D-sorbitol solution was added, and then, glycerin in which CMC-Na, sodium polyacrylate, aluminum chloride, tartaric acid, methylparaben and propylparaben were dispersed was added. The mixture was kneaded sufficiently until it became uniform to give a drug reservoir.

The drug reservoir was spread on a sheet of non-woven fabric at 1,000 g/m², and was covered with a protective film. Then, it was cut into an appropriate size to make transdermal patches (pH 7.1).

COMPARATIVE EXAMPLE 1

A gel type ointment

| | |
|---|---|
| 4-biphenylacetic acid | 3 g |
| polyacrylate copolymer | 1 g |
| diisopropanolamine | 3 g |
| ethanol | 3.5 g |
| purified water | q.s. 100 g |

The polyacrylate copolymer was swollen in a mixture of 20 g of purified water and the ethanol. Separately, diisopropanolamine and 4-biphenylacetic acid were dissolved in 10 g of purified water. The above two solutions were mixed, and the rest of purified water was added. The mixture was stirred until it became uniform to give a gel-type ointment.

COMPARATIVE EXAMPLE 2

A conventional transdermal patch

| | |
|---|---|
| 4-biphenylacetic acid | 1 g |
| sodium polyacrylate | 5 g |
| CMC-Na | 3 g |
| diethanolamine | 3 g |
| tartaric acid | 0.5 g |
| aluminum hydroxide hydrate | 0.2 g |
| methylparaben | 0.1 g |
| butylparaben | 0.1 g |
| purified gelatin | 3 g |
| propylene glycol | 5 g |
| glycerin | 25 g |
| purified water | q.s. 100 g |

To a solution of purified gelatin in 45 g of purified water, added was glycerin in which CMC-Na and aluminum hydroxide hydrate were dissolved, the resultant mixture was stirred. To the mixture, added were a solution of methylparaben and butylparaben in propylene glycol, and glycerin in which sodium polyacrylate and tartaric acid were dispersed, and then the mixture was kneaded. To the resultant mixture, diethanolamine and 4-biphenylylacetic acid dissolved in the rest of purified water were added. The mixture was kneaded to give a drug reservoir.

The drug reservoir was spread on a sheet of non-woven fabric at 1,000 g/m², and was covered with a protective film. Then, it was cut into an appropriate size to make transdermal patches (see referenced Japanese Patent Publication No. 85913/1989).

COMPARATIVE EXAMPLE 3

| | |
|---|---|
| 4-biphenylacetic acid | 1 g |

-continued

| | |
|---|---|
| diisopropanolamine | 3 g |
| sodium polyacrylate | 2 g |
| purified gelatin | 1 g |
| polyvinyl alcohol | 0.5 g |
| polyacrylate copolymer | 2.5 g |
| glycerin | 20 g |
| D-sorbitol solution | 20 g |
| aluminum hydroxide hydrate | 0.5 g |
| tartaric acid | 0.3 g |
| methylparaben | 0.1 g |
| propylene glycol | 0.05 g |
| purified water | q.s. 100 g |

A drug reserver without crotamiton was prepared in substantially the same manner as described in Example 1. The drug reservoir was spread on a sheet of non-woven fabric at 1,000 g/m², and was covered with a protective film. Then, it was cut into an appropriate size to make transdermal patches (pH 7.2).

The excellent pharmacological effects of the present invention are demonstrated by the following comparative tests.

Test 1; Effect of inhibiting carrageenin-induced paw edema (a) Experimental animals:

Wister strain male rats (body weight: 140-160 g), 10 per group.

(b) Test samples:

Those transdermal patches prepared in Examples 1, 2, 3 and Comparative Example 2 (3×3 cm² in size) were administered to the experimental animals (one per animal).

The gel-type ointment prepared in Comparative Example 1 was administered at a rate of 200 mg per test animal.

(c) Test procedure:

The volume of the left hind paw of each rat was measured with a plethysmometer.

The test patches were applied to the left hind paw of each rat. At 4 hours after the application, a 0.1 ml carrageenin solution (1%) as an inflammation inducer was injected subcutaneously at the application side to induce paw edema. The volume of the paw of the rat was measured at 2, 3 and 4 hours after the carrageenin injection. The endema rate is expressed by the % increase in the paw volume.

The rats of the gel-type ointment-applied group were administered the ointment at 2 and 4 hours before the injection of carragenin.

(d) Test results:

The test results are shown in FIG. 1. The transdermal patches of this invention showed a significantly superior edema inhibitive effect to that of the conventional patch (the product of Comparative Example 2).

Test 2; The measurement of 4-biphenylylacetic acid concentration in rat plasma (1)

(a) Experimental animals:

Wister strain male rats (body weight: 140-160 g), 5 per group.

(b) Test samples:

The transdermal patches prepared in Examples 1, 2, 3 and Comparative Example 2 (3×3 cm² in size) were administered to the test animals (one per animal).

The gel-type ointment prepared in Comparative Example 1 was administered to another group of the test animals at a rate of 100 mg per animal.

(c) Test procedure:

The transdermal patch or gel-type ointment was applied to the epilated back of those rats. Then 4-biphenylylacetic acid concentration in heir plasma was measured by HPLC method immediately thereafter, and at 1, 3, 6, 12 and 24 hours after the application.

The patches were removed at 12 hours after the application, while the gel-type ointment was left intact.

Figure 2:
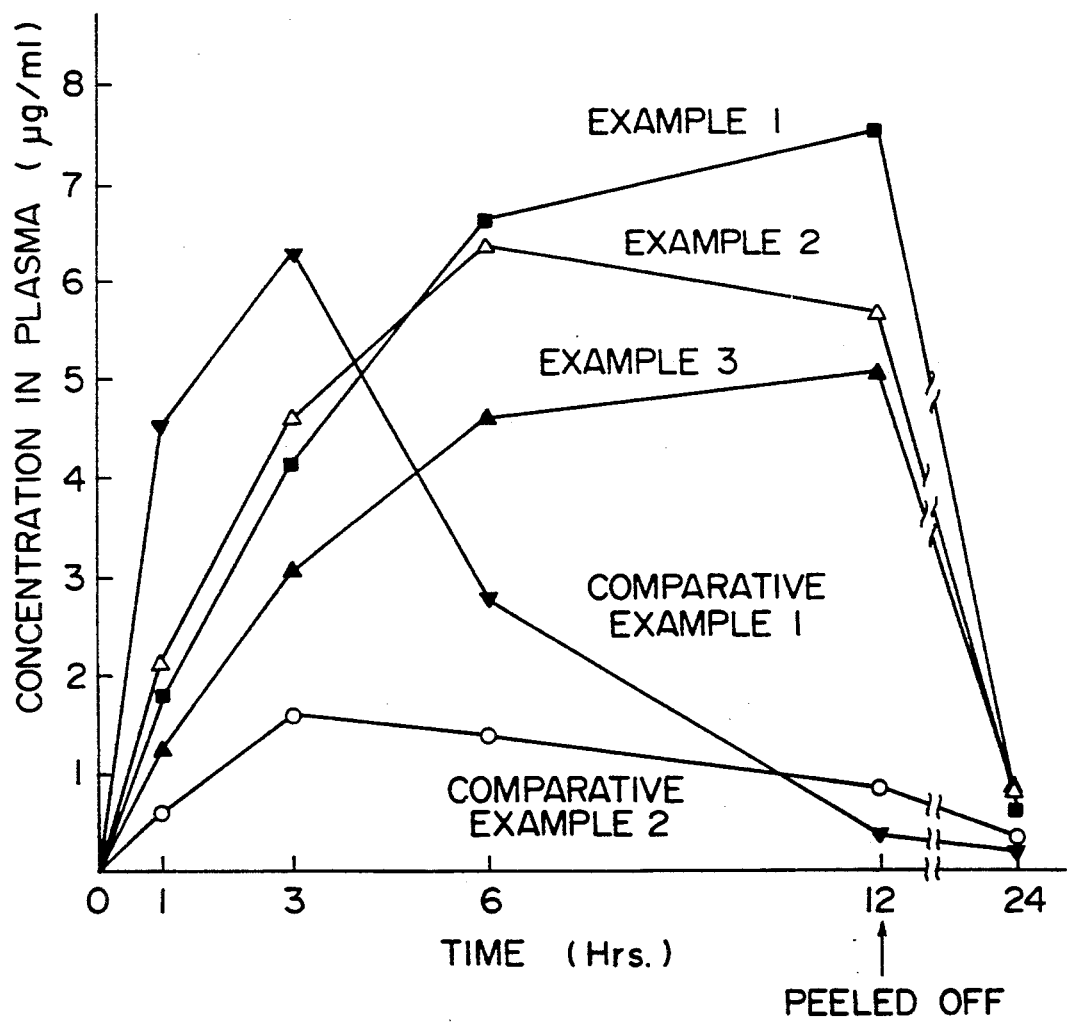
FIG. 2 shows the 4-biphenylylacetic acid concentrations ($\mu$g/ml) in rat plasma measured in Test 2.

(d) Test results:

The test results are shown in FIG. 2. All patches of the present invention showed a higher concentrations of 4-biphenylylacetic acid in plasma, compared to the conventional patch (the product of Comparative Example 2). And the patches of the present invention maintained sufficiently high concentration of 4-biphenylylacetic acid in plasma even 12 hours after the application, which indicates that it bioavailability is remarkably superior to those of conventional ointment and patch.

Test 3; The measurement of 4-biphenylylacetic acid in rat plasma (2)

(a) Experimental animals:

Wister strain male rats (body weight: 140–160 g), 5 per group.

(b) Test samples:

The patches prepared in Example 1 and Comparative Example 3, (3×3 cm² in size) were administered to the experimental animals (one per animal).

The gel-type ointment prepared in Comparative Example 1 was administered at a rate of 200 mg per test animal.

(c) Test procedure:

The 4-biphenylylacetic acid concentration in rat plasma was measured in substantially the same manner as described in Test 2.

Tested patches were removed at 12 hours after application.

Figure 3:
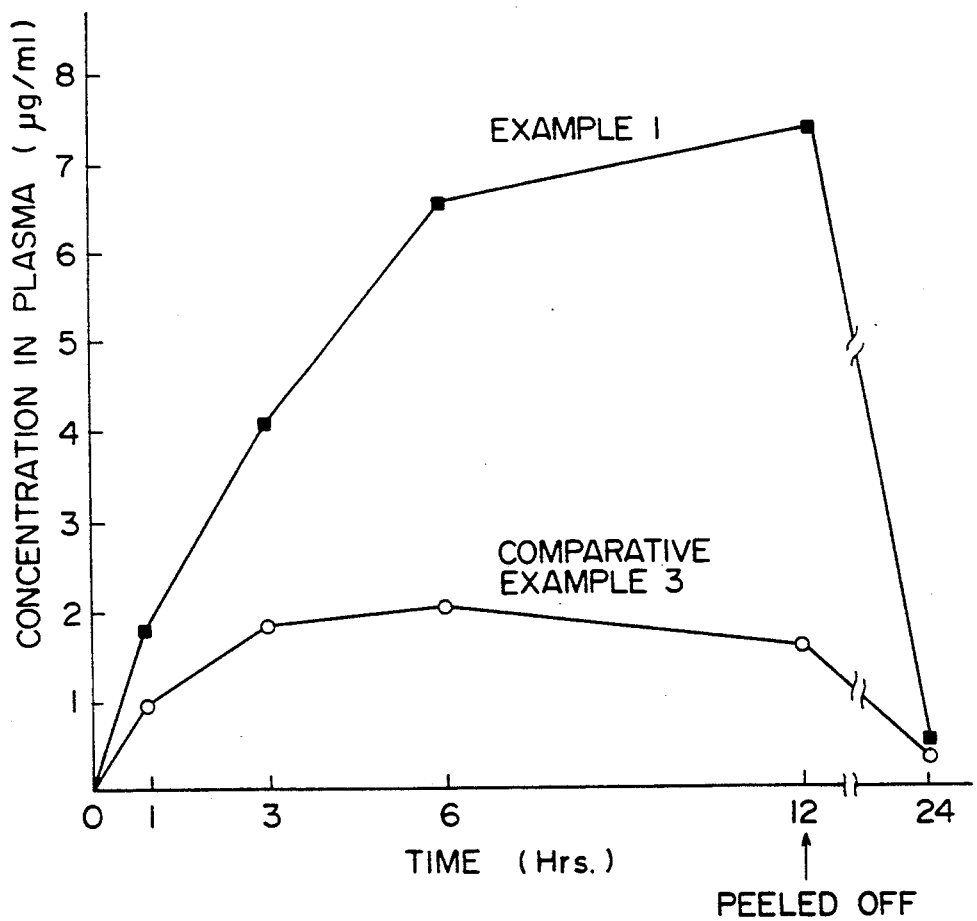
FIG. 3 shows the 4-biphenylylacetic acid concentrations ($\mu$g/ml) in rat plasma measured in Test 3.

(d) Test results:

The test results are shown in FIG. 3. The patches of Comparative Example 3 contained no crotamiton.

The patch containing crotamiton (Example 1) showed higher concentration of 4-biphenylylacetic acid in plasma of the experimental rats compared with that of the rats applied with the patch without crotamiton (Comparative Example 3).

Test 4; Tackiness stability test of patches

The patches prepared in Examples 1 to 3 and Comparative Example 2 as a control were subjected to a tackiness stability test.

(a) Test procedures:

Test samples were stored at 40° C., 75% (humidity) for 0, 1, 2 and 4 months, and the changes in their adhesive strength was examined.

The adhesive strength was tested by the method described in "DRUG APPROVAL AND LICENSING PROCEDURES IN JAPAN 1989", p62.

According to the standard in the above reference, the adhesive strength was evaluated on the basis of diameter of steel balls which stopped on the adhesive surface of each test sample.

(b) Test results:

The test results are shown in Table 1.

TABLE 1

| Test samples | Period of storage (month) | | | |
| --- | --- | --- | --- | --- |
| | 0 | 1 | 2 | 4 |
| Control | stop (9.5 mm*) | non-stop (3.2 mm) | non-stop (3.2 mm) | non-stop (3.2 mm) |
| Example 1 | stop (11.1 mm) | stop (9.5 mm) | stop (9.5 mm) | stop (9.5 mm) |
| Example 2 | stop (11.1 mm) | stop (9.5 mm) | stop (9.5 mm) | stop (9.5 mm) |
| Example 3 | stop (11.1 mm) | stop (9.5 mm) | stop (9.5 mm) | stop (9.5 mm) |

*diameter of steel ball

The patches prepared in Examples 1 to 3 of this invention showed excellent adhesive strength after storage at 40° C., 75% (humidity) for 4 months.

In contrast, the adhesive strength of the control patch became weaker after 1 month storage, and its drug reservoir became harder.

What we claim is:

1. An anti-inflammatory analgesic dosage unit for transdermal application in the form of a patch having (i) a drug-reservoir layer comprising an effective anti-inflammatory amount of 4-biphenylacetic acid to provide an analgesic effect; (ii) a polymer of acrylic acid, (iii) at least 0.05 parts by weight crotamiton per 100 parts by weight 4-biphenylacetic acid within said drug-reservoir, and (iv) 0.5 to 15% by weight water-soluble organic amine based on the weight of the drug-reservoir and 0.1 to 5% organic acid based on the weight of the drug-reservoir, said water-soluble organic amine and said organic acid being adjusted whereby said drug-reservoir is maintained at a pH in the range of 6 to 8.

2. The patch of claim 1, in which the water-soluble organic amine is a mono-, di- or tri-(lower alkanolamine).

3. The patch of claim 2, in which the water-soluble organic amine is diisopropanolamine, triethanolamine or diethanolamine.

4. The patch of claim 1, in which the organic acid is selected from malic acid, tartaric acid, citric acid, gluconic acid, lactic acid and oleic acid.

5. The patch of claim 1, in which the pH of the drug reserver is within a range of 6.3 to 7.5.

6. The patch of claim 1 which contains 0.1 to 5% by weight of 4-biphenylylacetic acid based on the weight of the drug reservoir.

7. An anti-inflammatory analgesic patch of claim 1 which includes a humectant.

8. An anti-inflammatory analgesic patch of claim 1 which includes a thickener.

9. An anti-inflammatory analgesic patch of claim 1 wherein said polymer is an acrylic acid homopolyer or copolymer or mixture thereof.

* * * * *